United States Patent
Sergheraert et al.

(10) Patent No.: US 7,399,481 B2
(45) Date of Patent: *Jul. 15, 2008

(54) METHODS FOR TREATING, MAINTAINING, OR IMPROVING FUR OR HAIR PIGMENTATION OF DOMESTIC CARNIVORES USING A COMPOSITION COMPRISING FREE TYROSINE

(75) Inventors: Renaud Sergheraert, Baden (FR); Vincent Biourge, Saint Nolff (FR); Mickaël Deboise, Vannes (FR)

(73) Assignee: Royal Canin S.A., Aimargues (FR)

( * ) Notice: Subject to any disclaimer, the term of this patent is extended or adjusted under 35 U.S.C. 154(b) by 668 days.

This patent is subject to a terminal disclaimer.

(21) Appl. No.: 10/633,237

(22) Filed: Jul. 31, 2003
(Under 37 CFR 1.47)

(65) Prior Publication Data
US 2004/0022829 A1 Feb. 5, 2004

Related U.S. Application Data

(63) Continuation of application No. 09/703,522, filed on Nov. 1, 2000, now Pat. No. 6,641,835.

(51) Int. Cl.
*A61K 47/00* (2006.01)
(52) U.S. Cl. .................. 424/439; 424/400; 424/442; 426/2; 426/74; 426/96; 426/805
(58) Field of Classification Search .......... 424/400, 424/439, 442; 514/567
See application file for complete search history.

(56) References Cited

U.S. PATENT DOCUMENTS

| | | | |
|---|---|---|---|
| 3,950,529 A | 4/1976 | Fischer et al. | |
| 4,265,913 A | 5/1981 | Eichelburg | |
| 4,282,254 A | 8/1981 | Franzen et al. | |
| 4,696,914 A | 9/1987 | Rüsse et al. | |
| 5,173,085 A | 12/1992 | Brown et al. | |
| 5,276,056 A | 1/1994 | LeRoy | |
| 5,310,539 A | 5/1994 | Williams | |
| 5,578,296 A | 11/1996 | Kashino et al. | |
| 5,942,531 A | 8/1999 | Diaz et al. | |
| 5,962,417 A | 10/1999 | Gilchrest et al. | |
| 2001/0014442 A1* | 8/2001 | Morris et al. | ......... 435/1.1 |

FOREIGN PATENT DOCUMENTS

| | | |
|---|---|---|
| EP | 0 026 985 | 4/1981 |
| EP | 0 210 420 | 6/1986 |
| EP | 0 862 910 A2 | 9/1998 |
| FR | 2 582 485 | 5/1985 |
| WO | WO 97/35998 | 10/1997 |
| WO | WO 01/58442 A1 | 8/2001 |

OTHER PUBLICATIONS

Slominski et al. "Positive regulation of melanin pigmentation by two key substrates of the melanogenic pathway, L-tyrosine and L-dopa." J Cell Sci. Mar. 1988;89 ( Pt 3):287-96.
Hearing et al. "Enzymatic control of pigmentation in mammals." FASEB J. Nov. 1991;5(14):2902-9.
Board on Agriculture. Nutrient Requirements of Cats, Revised Edition, 1986, p. 42 (online: http://books.nap.edu/openbook.php?isbn=0309036828&page=42).
Board on Agriculture. Nutrient Requirements of Dogs, Revised, 1985, p. 12 (online: http://books.nap.edu/openbook.php?isbn=0309034965&page=12).
Case et al. Canine and Felice Nutrition. Mosby-Year Book, Inc. 1995, pp. 316-319.
GNLD, "Introduction to aminio acids." Products—Jun. 1999 (online: wwl.gnld.com/pages/businessguide_cd1005/gnldbustools_web/content/pdf/products/weight_loss/AminoAcid.pdt).
Lexikon der Sporternährung (online: http://www.fitshop.de/forum/lex/lexikon/lexikonA.htm) (with English translation).
Watson TD. "Diet and skin disease in dogs and cats." J Nutr. Dec. 1998;128(12 Suppl):2783S-2789S.
Hand et al. Small Animal Clinical Nutrition. 4th Ed. Mark Morris ASsociates, Jul. 1998, pp. 51-56.

* cited by examiner

*Primary Examiner*—Shelley A. Dodson
(74) *Attorney, Agent, or Firm*—Jones Day

(57) ABSTRACT

The present invention relates to a food composition for domestic carnivores which makes it possible to prevent or correct pigmentation abnormalities and/or to improve the quality of the fur of the said domestic carnivores, characterized in that it contains a source of free tyrosine representing at least 5% of the total tyrosine supplied. The invention also relates to a method for preventing or correcting pigmentation abnormalities of the fur of domestic carnivores that uses said food composition.

24 Claims, No Drawings

METHODS FOR TREATING, MAINTAINING, OR IMPROVING FUR OR HAIR PIGMENTATION OF DOMESTIC CARNIVORES USING A COMPOSITION COMPRISING FREE TYROSINE

This application is a continuation of U.S. application Ser. No. 09/703,522, filed Nov. 1, 2000, now U.S. Pat. No. 6,641,835, which claims the priority of French Application No. FR 9913657, filed Nov. 2, 1999, which applications are incorporated herein by reference in their entirety.

The present invention relates to a food composition for domestic carnivores which makes it possible to prevent or correct pigmentation abnormalities and/or to improve the quality of the fur of the said domestic carnivores, characterized in that it contains a source of free tyrosine representing at least 5% of the total tyrosine supplied. The invention also relates to a veterinary composition containing tyrosine, as well as the use of free tyrosine for the preparation of a food and/or veterinary composition intended for preventing pigmentation abnormalities and/or for improving the quality of the fur in a domestic carnivore.

Despite a rich and nutritionally well-balanced diet, in particular as regards the supply of proteins and amino acids, many breeders or owners of domestic carnivores, particularly dogs and cats, complain of abnormalities in the pigmentation of their animals.

These "discolorations" cause them substantial financial losses, particularly during competitions, the animals displaying these abnormalities being systematically downgraded or even eliminated by "judges" who know the "standards" of each breed of animal well.

Domestic carnivores designate dogs and cats, but also other animal species, and particularly animals having a coat, mink, fox, sable and the like.

These poor pigmentations may occur in the skin, the mucous membranes, the eyes, and more frequently in the hair.

The normal colour of these organs is the visual result of the deposits of several sorts of pigments:

nonmelanic pigments: blood pigments (oxyhaemoglobin, reduced hemoglobin, haemosiderin), carotene and its derivatives;

melanic pigments or melanins (eumelanins, phaeomelanins, trichochromes) (E. Guaguère et al., Le Point Vétérinaire, 1985, vol. 17, No. 93, 549-557).

Among these pigments, it is mainly the eumelanins which give the black colour or the dark shade of the pigmentation of the organs.

It is known that the melanins are synthesized by organelles called melanosomes of the specialized cells called melanocytes, from tyrosine, a "semi-essential" aromatic amino acid supplied by the dietary proteins. An amino acid is said to be "essential" when it is necessarily supplied by a source which is external to the animal, because the latter itself does not know how to produce it. Thus, tyrosine is "semi-essential" because the animal can synthesize it from another "essential" aromatic amino acid, phenylalanine. Consequently, for example, the National Research Council (N.R.C.) of the United States of America, which is the world authority on animal nutrition, recommends the following nutritional standards for cats and dogs, based on the dry matter content of the foods, and of which only phenylalanine is considered as being essential (Nutrient Requirements of Cats, 1986; Nutrient Requirements of Dogs, 1985):

|  | Cats | Dogs |
| --- | --- | --- |
| Proteins | 240 g/kg (that is 24%) | Not indicated |
| Phenylalanine + tyrosine | 8.5 g/kg (that is 0.85%) | 0.72% |
| Of which phenylalanine | 4 g/kg (that is 0.4%) | ≧50% of Phe + Tyr |

These standards have nevertheless currently been widely overtaken by balanced industrial foods which are considerably richer in proteins and in amino acids, and have consequently already a high content of tyrosine.

Yet, in spite of the richness of the current foods supplied by all the major international brands, breeders frequently complain of the pigmentation abnormalities in their animals, and particularly in their fur. Breeders and vets speak in this case of "decolorization", of "discoloration", of "depigmentation", of "dispigmentation", of "red hair", of "yellow hair", of "faded hair", and the like, to designate this syndrome.

The nutritional etiology of this syndrome is commonly excluded by vets and nutritionists (L. Case et al., Canine and Feline Nutrition, 1995, Mosby Ed., Saint Louis, USA, p 316-319). Particularly, Paragon and Granjean (Rec. Vét. Méd., 1992168(10), 769-77) have excluded a possible deficiency of tyrosine in dogs and cats normally fed in practical conditions.

Only one team in the Ecole Nationale Vétérinaire de Toulouse has described in dogs a "rubra-pilaris syndrome" or red hair disease which can have a nutritional cause (P. Dorchies et al., Revue de Médecine Vétérinaire, 1979, 130 (10), 13711382). Indeed, the syndrome is accompanied by an increase in the level of blood and urinary indican. This high presence of indican in the blood and the urine is a sign of a poor digestive use of an essential amino acid, tryptophan, because indican or potassium indoxylsulphate is a metabolite which is synthesized by the bacteria in the large intestine from dietary tryptophan.

The applicant has discovered that this phenomenon of pigmentation abnormality is due to a deficiency in free tyrosine in the diet.

The applicant has indeed discovered that in order to prevent pigmentation abnormalities and/or correct them when they exist in domestic carnivores fed with current balanced foods which have aromatic amino acids, in particular tyrosine, supplied well above the known recommended standards (such as those of N.R.C., for example), it is essential that part of the tyrosine is supplied to the animal in free form and that the tyrosine supply does not exist solely and completely in bound tyrosine form. This discovery is valid regardless of the level of aromatic amino acid contents in the foods, provided that they are equal to or above the recommended nutritional standards.

Conventionally, an amino acid is said to be "bound" when it is embedded in the structure of a protein. To be able to assay a bound amino acid, the protein should be previously and completely hydrolyzed, most often with a protease or a strong acid or a strong base. This is the case for the amino acids supplied by the proteins in the dietary raw materials commonly used, whether they are of animal or plant or microbial or fungal origin.

An amino acid is said to be "free" when its assay does not require prior hydrolysis with a protease or a strong acid or a strong base. To assay a free amino acid in a food, it must simply be separated from the structured proteins by precipitating them, with a protein coagulant such as trichloroacetic acid or sulphosalicylic acid for example. After separating the structured proteins, the free amino acid can then be assayed by any known means, such as liquid chromatography for example.

The applicant has discovered, surprisingly, that when at least 5% of the total supplied tyrosine, and still more preferably at least 10%, 15%, 20%, 25% or 30% is supplied to the animal in free form, it is possible to prevent the pigmentation abnormalities in domestic carnivores and/or to treat them when they exist. It is necessary for the free tyrosine to be supplied to the animal, regardless of the quantity of bound tyrosine supplied.

Thus, the invention relates to a domestic carnivore food composition for preventing pigmentation abnormalities and/or improving the quality of the fur, characterized in that it contains:

- at least one source of proteins of animal or plant origin, and/or
- at least one source of fatty substances of animal or plant origin, and/or
- at least one source of rapid or slow carbohydrates, in particular cereals, and
- one source of free tyrosine representing at least 5% of the total tyrosine supplied.

In another embodiment of the invention, the free tyrosine level in the food composition will be greater than 10% of the total tyrosine supplied.

In another embodiment, the food composition already contains a level of tyrosine that is well above the nutritional standards as mentioned above.

The invention also relates to a domestic carnivore veterinary composition for preventing pigmentation abnormalities and/or improving the quality of the fur, characterized in that it contains a source of free tyrosine representing at least 5%, and preferably at least 10%, 15%, 20%, 25% or 30% of the total tyrosine supplied in the diet.

The applicant has therefore developed a method for preventing pigmentation abnormalities and/or improving the quality of the fur in domestic carnivore, characterized in that a quantity of free tyrosine greater than 5%, or preferably 10%, 15%, 20%, 25% or 30% of the quantity of total tyrosine supplied in the diet of the said carnivore is administered to the said carnivore. This process, notably for its esthetic result, is also one of the subjects of the present invention.

The food compositions according to the invention may be dry foods such as biscuits for example, semi-moist foods, for example pates and the like, or moist foods. These foods also comprise snacks, treats or extruded foods, as well as nutritional supplements.

The veterinary compositions according to the invention include compositions which can be administered by the oral, parenteral or dermal route. Preferably, the veterinary composition will be administered by the oral or parenteral route or by the gastrodigestive system. Thus, the veterinary composition according to the invention may be in particular, without this list being limiting, an intragastric, intraintestinal, intramuscular, subcutaneous or intravenous infusion, a hard gelatin capsule, a pill, a soft gelatin capsule, a bolus, a suppository or any other presentation which can be administered by the digestive route.

Conventional excipients may be added to this veterinary composition, such as gelatin, starch, lactose, magnesium stearate, talc, gum arabic and the like.

The free tyrosine supply may consist of L-tyrosine and/or its salts. Commercially available L-tyrosine may be obtained by extraction after enzymatic or chemical hydrolysis of various animal, plant, microbial or fungal proteins or by any other process known to amino acid producers. It is also possible to use as free tyrosine source a protein which is completely or partially hydrolyzed (with a protease, an acid or a base), whether the original protein is of animal, plant, microbial or fungal origin, without the free tyrosine being separated from the rest of the amino acids.

The applicant has also discovered that, particularly in the fur of animals, the supply of free tyrosine improves not only the pigmentation but also the quality of the fur, mainly the density and the length of the hair.

The examples which follow are intended to illustrate some aspects of the invention without, however, being limiting.

EXAMPLES

Example 1

The protein, free tyrosine and bound tyrosine levels of dog and cat foods representative of the well known brands on the world market are assayed. The assays were performed according to the standard methods of the Laréal laboratory, 56250 Saint Nolff, France which is accredited by the French Committee on Accreditation more generally known under the name COFRAC (Accreditation Number: 1 285). Particularly, the bound tyrosine and the free tyrosine were assayed according to the AFNOR (Association Française de Normalisation) standard method XP V 18-113 (January 1988).

The assays showed that no free tyrosine is present in the commercially available foods. Only bound tyrosine could be assayed.

The results obtained on the crude foods are the following:

|  | Proteins (%) | Bound tyrosine (%) |
|---|---|---|
| Dog foods: | | |
| Eukanuba Puppy | 31.1 | 1.04 |
| Eukanuba Junior | 26.1 | 0.85 |
| Eukanuba Premium | 30.3 | 1.02 |
| Eukanuba Regular | 27.6 | 0.82 |
| Hill's Growth | 25.6 | 0.95 |
| Hill's Maintenance | 22.8 | 0.87 |
| Hill's M. Light | 16.1 | 0.57 |
| Hill's Senior | 16.2 | 0.56 |
| Proplan Puppy | 29.3 | 1.25 |
| Proplan Adult | 26.5 | 1.05 |
| Proplan Light | 26.9 | 1.02 |
| Proplan Senior | 25.6 | 0.93 |
| Royal Canin Mini Junior | 32.8 | 0.92 |
| Royal Canin Adult 1 | 27.5 | 0.83 |
| Royal Canin Adult 2 | 27.4 | 0.80 |
| Royal Canin Medium Junior | 25.7 | 0.79 |
| Royal Canin Medium Adult 1 | 25.7 | 0.81 |
| Royal Canin Medium Adult 2 | 25.6 | 0.81 |
| Royal Canin Maxi Junior | 35.7 | 0.98 |
| Royal Canin Maxi Adult 1 | 25.5 | 0.75 |
| Royal Canin Maxi Adult 2 | 26.2 | 0.78 |
| Cat foods: | | |
| Iams Chicken | 32.6 | 1.11 |
| Iams Kitten | 34.1 | 1.06 |
| Hill's Growth | 34.7 | 1.29 |
| Hill's Maintenance | 31.2 | 1.12 |
| Hill's Senior | 29.9 | 1.23 |
| Proplan Kitten | 33.7 | 1.23 |
| Proplan Adult | 33.5 | 1.39 |
| Proplan Light | 33.9 | 1.49 |
| Royal Canin Kitten 34 | 33.1 | 1.04 |
| Royal Canin Sensible 33 | 33.1 | 1.07 |
| Royal Canin Senior 28 | 28.6 | 1.11 |

These results show that the commercially available dog and cat foods are very rich and widely exceed the standards recommended by N.R.C., mainly for the tyrosine supplies. However, in all these foods, the tyrosine exists completely in the bound form.

Example 2

An experimental complete food for domestic carnivores, presented in the form of extruded foods, and in which the composition of the raw materials is the following (%), was manufactured:

| | | |
|---|---|---|
| | Animal proteins | 31 |
| | Rice | 24 |
| | Maize | 5 |
| | Vegetable by-products | 13.6 |
| | Fats and oils | 16.2 |
| | Flavourings | 4 |
| | Fishmeal | 2 |
| | Vitamin-mineral premixes | 4 |
| | Commercially available L-tyrosine | 0.2 |
| | Total | 100 |

The L-tyrosine provided by the company B.C.F., 56140 Pleucadeuc, France, has a free tyrosine titre of 97%, which means that 0.2% provides 0.19% of free tyrosine in the food.

The analytical characteristics of the food are the following:

| | | |
|---|---|---|
| | Proteins | 30% |
| | Fatty substances | 22% |
| | Calcium | 0.80% |
| | Phosphorus | 0.75% |
| | Cellulose | 4.50% |
| | Metabolizable energy | 4340 kcal/kg |
| | Phenylalanine | 1.30% |
| | Bound tyrosine | 1.04% |
| | Free tyrosine | 0.19% |
| | Total tyrosine (bound + free) | 1.23% |
| | (Free tyrosine/total tyrosine) × 100 | 15.4% |

This experimental food was distributed to cats on two specialized farms. At the end of the trials which lasted for 6 months on the first farm and 4 months on the second farm, the observations on the fur of the animals, made by specialist breeders and experienced technicians, are the following, with respect to the desired standards for these animals:

| Farm | Number of cats | Pigmentation | Qualities of the fur | Length of the hair |
|---|---|---|---|---|
| M . . . | 5 | Very black, without any discoloration | Dense | Long |
| C . . . | 7 | Dark, intense, without any discoloration | Dense, soft to the touch, easy to disentangle | Long |

These results show that the experimental food, during many months of trials, prevented any problem of discoloration which is often found on this type of specialized farms from occurring. In the same manner, the qualities of the fur were judged to have improved compared with cats fed with the previously used foods, which are commercially available foods containing no free tyrosine.

Example 3

A 7-year-old female cat of "Tricolour Persian" breed was fed with commercially available foods containing no free tyrosine. This female cat exhibited abnormalities in its fur compared with the standards for its breed: "faded" black hair and excess of "reddish yellow" hair.

The experimental food of Example 2, containing free tyrosine, was given to this female cat. After four and a half months of trial, the "faded hair" become dark and the "reddish yellow" hair defect decreased.

This example shows that a food containing free tyrosine was able to correct the pigmentation abnormalities in a domestic carnivore.

Example 4

Four black-haired cats, were suffering of the "red hair syndrome", while being fed with the commercial diet S9 Felistar® (originating from Royal Canin).

Analysis of this food composition shows that it is a balanced food very rich in protein content and that the level of tyrosine is well above the recommended needs for cats:

| | | |
|---|---|---|
| | Proteins | 31% |
| | Tyrosine | 1.10% |

Further analysis of this food shows that the tyrosine is coming exclusively from the structured proteins of the raw materials. The tyrosine present in this food is therefore completely "bound".

After a detailed veterinary examination, these cats received the same food composition, enriched in free tyrosine. The levels of the different forms of tyrosine in this composition are as follow:

| | | |
|---|---|---|
| | Bound tyrosine | 1.10% |
| | Free tyrosine | 0.43% |
| | Total tyrosine | 1.53% |

The colors of the cats' coats were as described in the following table:

| | | | Color of the coat | | | | | |
|---|---|---|---|---|---|---|---|---|
| Cat | Sex | Age (Years) | Day 0 | Day 28 | Day 59 | Day 98 | Day 134 | Day 212 |
| Charbon | M | 9 | R | R | R | B | B | B |
| Jeep | M | 6 | R | B | B | B | B | B |
| Iris | F | 7 | R | B | N.A. | B | B | N.A. |
| Fida | F | 8 | R | B | B | B | N.A. | N.A. |

M = male, F = female, R = red, B = black, N.A. = non available

These results show that addition of free tyrosine in a commercial diet leads to an improvement in the color of the coat of cats suffering from the "red hair syndrome".

We claim:

1. A domestic carnivore food composition for treating or correcting pigmentation abnormalities and/or improving the quality of the fur, comprising:
at least one source of protein of animal or plant origin, and/or at least one source of fatty substances of animal or plant origin, and/or at least one source of carbohydrates, and one source of free tyrosine representing at least 5% by weight of the total tyrosine supplied in the food composition.

2. The food composition of claim 1, wherein the free tyrosine level is greater than 10% of the total tyrosine supplied in the food composition.

3. The food composition of claim 1, wherein the domestic carnivore is chosen from cats, dogs, minks, foxes or sables.

4. The food composition of claim 1, wherein the amount of free tyrosine is at least 10%, 15%, 20%, 25%, or 30% by weight of the total amount of tyrosine in the food composition.

5. The food composition of claim 1, wherein the food composition is a cat food composition.

6. The food composition of claim 1, wherein the food composition is a dog food composition.

7. The food composition of claim 1, wherein the food composition is a mink food composition, a fox food composition, or a sable food composition.

8. The food composition of claim 1, wherein the color of the hair or fur is black.

9. The food composition of claim 5, wherein the cat food composition meets the standard of Nutrient Requirements of Cats as published by the National Research Council of the United States of America.

10. The food composition of claim 6, wherein the dog food composition meets the standard of Nutrient Requirements of Dogs as published by the National Research Council of the United States of America.

11. The food composition of claim 1, wherein the food composition has a level of amino acids equal to or above acceptable nutritional standards.

12. The food composition of claim 1, wherein the food composition is a nutritionally well-balanced food composition.

13. The food composition of claim 1, further comprising a source of bound tyrosine.

14. The food composition of claim 13 wherein the bound tyrosine is in the source of protein.

15. A domestic carnivore food composition for treating or correcting pigmentation abnormalities and/or improving the quality of the fur, comprising:

(a) a source of bound tyrosine; and (b) a source of free tyrosine, wherein the amount of free tyrosine is at least 5% by weight of the total amount of tyrosine in the food composition.

16. The food composition of claim 15 wherein the amount of free tyrosine is at least 10%, 15%, 20%, 25%, or 30% by weight of the total amount of tyrosine in the food composition.

17. The food composition of claim 15 wherein the food composition is a cat food composition.

18. The food composition of claim 15 wherein the food composition is a dog food composition.

19. The food composition of claim 15 wherein the food composition is a mink food composition, a fox food composition, or a sable food composition.

20. The food composition of claim 15 wherein the color of the hair or fur is black.

21. The food composition of claim 17 wherein the cat food composition meets the standard of Nutrient Requirements of Cats as published by the National Research Council of the United States of America.

22. The food composition of claim 18 wherein the dog food composition meets the standard of Nutrient Requirements of Dogs as published by the National Research Council of the United States of America.

23. The food composition of claim 15 wherein the food composition has a level of amino acids equal to or above acceptable nutritional standards.

24. The food composition of claim 15 wherein the food composition is a nutritionally well-balanced food composition.

* * * * *